US00PP30152P2

(12) United States Plant Patent
Jones

(10) Patent No.: US PP30,152 P2
(45) Date of Patent: Jan. 29, 2019

(54) ***DIANTHUS* PLANT NAMED 'DCACA06-0'**

(50) Latin Name: *Dianthus hybrida*
Varietal Denomination: DCACA06-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 15/731,662

(22) Filed: Jul. 12, 2017

(51) Int. Cl.
*A01H 5/02* (2018.01)

(52) U.S. Cl.
USPC ..... Plt./273

(58) Field of Classification Search
USPC ..... Plt./276, 277, 272, 273, 281, 282
CPC ..... A01H 5/02; A01H 5/0233; A01H 5/0255; A01H 6/305; A01H 6/30
See application file for complete search history.

(56) References Cited

PUBLICATIONS

Issuu Michell's Products Catalog 2017, published on Aug. 10, 2016, retrieved on Jun. 13, 2018, retrieved from the Internet at https://issuu.com/hfmichell/docs/2017michellscatalog-pf, cover page, pp. 2, 52, 112-113. (Year: 2016).*

Johnson Nursery Corporation for *Dianthus* Cadence Raspberry, retrieved on Jun. 13, 2018, retrieved from the Internet at http://www.johnson-nursery.com/plant-nursery-new/plant/dianthus-cadence-raspberry/id/3599834, one page. (Year: 2018).*

* cited by examiner

*Primary Examiner* — June Hwu
(74) *Attorney, Agent, or Firm* — Cassandra Bright

(57) ABSTRACT

A new and distinct *Dianthus* cultivar named 'DCACA06-0' is disclosed, characterized by continuous flowering on floriferous plants hardy to USDA Zone 3. Flowers are double and medium pink to purple. The new variety is a *Dianthus*, typically produced as a garden or container plant.

2 Drawing Sheets

Latin name of the genus and species: *Dianthus hybrida.*
Variety denomination: 'DCACA06-0'.

BACKGROUND OF THE INVENTION

The new cultivar is a product of chance discovery. The new variety originated as a spontaneous whole plant mutation discovered among a commercial planting of mixed *Dianthus hybrida* varieties. The parent is unknown. 'DCACA06-0' was discovered by the inventor, Steve Jones, at a commercial greenhouse in Santa Paula, Calif. during Summer of 2014.

Asexual reproduction of the new cultivar 'DCACA06-0' was first performed in Santa Paula, Calif. at a commercial greenhouse by terminal vegetative cuttings in Summer of 2014. 'DCACA06-0' has since produced several generations and has shown that the unique features of this cultivar are stable and reproduced true to type.

SUMMARY OF THE INVENTION

The cultivar 'DCACA06-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCACA06-0'. These characteristics in combination distinguish 'DCACA06-0' as a new and distinct *Dianthus* cultivar:

1. Floriferous plants.
2. Suitability for both garden and container uses.

3. Medium pink to purple flower colored near Red-Purple 71B and Purple 75A.
4. Continuous flowering from Spring through Fall. Repeat flowering enhanced by removal of spent flowers.
5. Hardy to USDA zone 3
6. Double flower with an average of 15 to 20 petals.

COMMERCIAL COMPARISON

Plants of the new cultivar 'DCACA06-0' are comparable to the commercial *Dianthus* variety 'DCACR08-0', U.S. Plant patent application Ser. No. 15/731,665, filed concurrently. The two *Dianthus* varieties are similar in most horticultural characteristics; however, the new variety 'DCACA06-0' produces a flower with a different red-purple color, mainly lighter and having more purple tones. Flowers of the new variety also do not fade with age as much as flowers of this comparator.

Plants of the new cultivar 'DCACA06-0' can also be compared to the commercial *Dianthus* variety 'DDTHP02-0', U.S. Plant Pat. No. 28,102. These varieties are similar in most horticultural characteristics; however 'DCACA06-0' produces a darker pink to purple flower than the flower of this comparator.

BRIEF DESCRIPTION OF THE PHOTOGRAPHS

Figure 1:
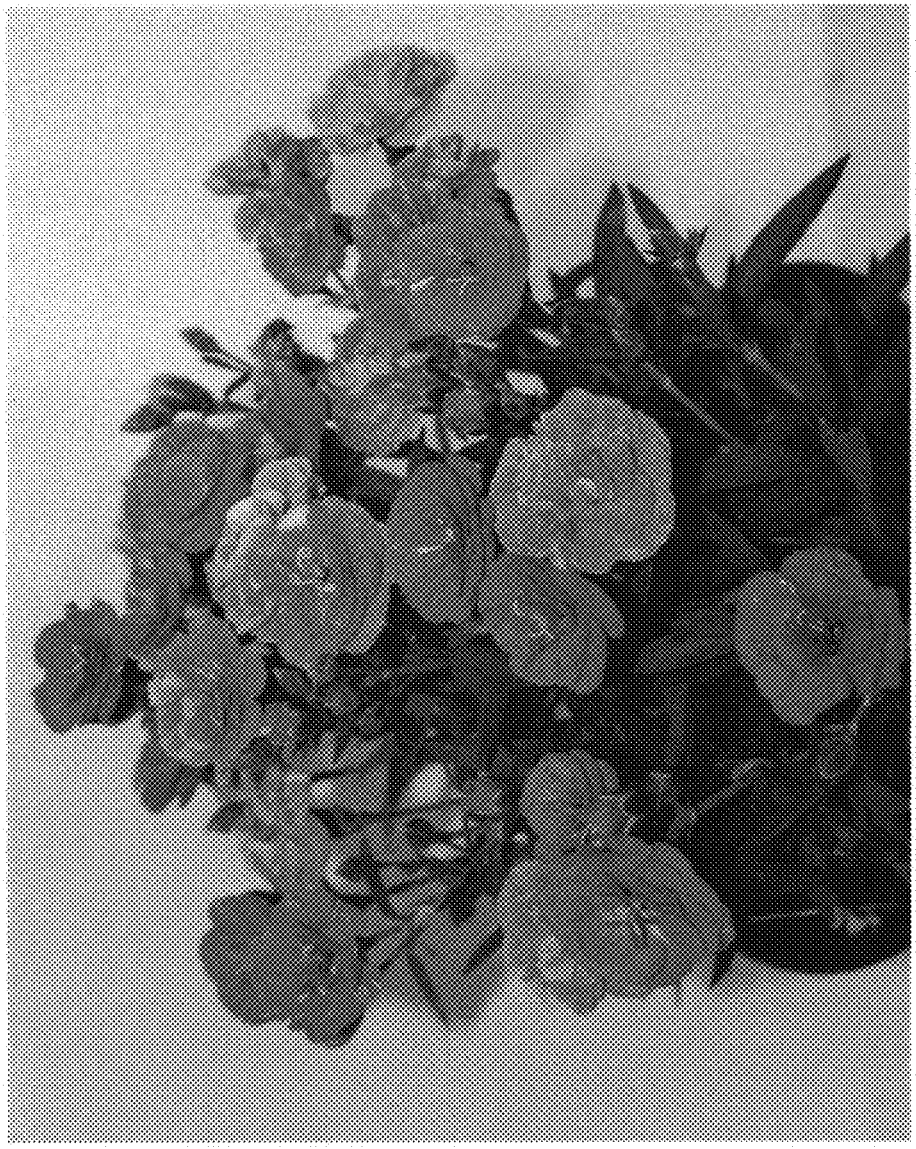

The accompanying photograph in FIG. 1 illustrates in full color a typical plant of 'DCACA06-0' grown outdoors in Santa Paula, Calif. This plant is approximately 20 weeks old, shown in a 1 gallon pot.

Figure 2:
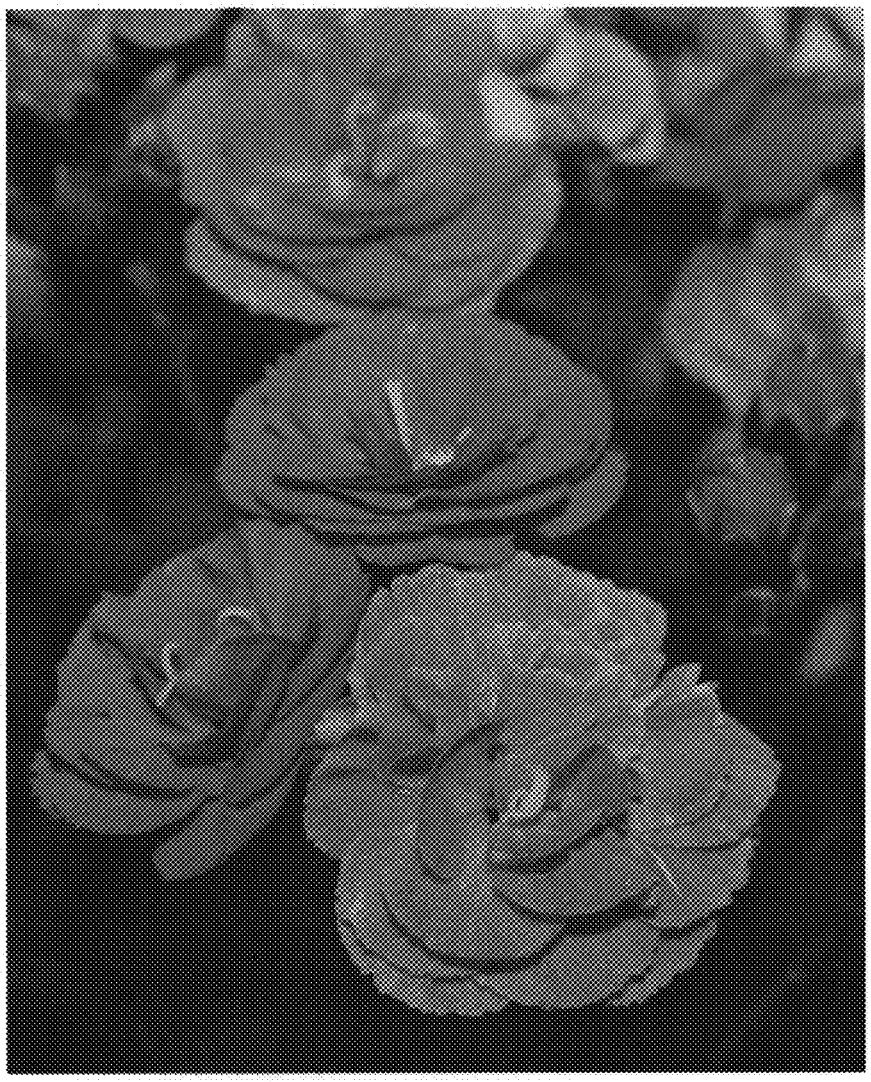

FIG. 2 illustrates a close up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'DCACA06-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus hybrida* 'DCACA06-0'.

PROPAGATION

Time to initiate roots: About 10 days at approximately 24° C.

Time to produce a rooted cutting: About 18 days at 24 ° C.

Root description: Fibrous roots, approximately 1 to 3 mm in diameter, colored near Orange-White 159C.

PLANT

Age of plant described: Approximately 20 weeks from rooted cutting.

Pot size: 1 gallon.

Plant type: Compact upright perennial.

Plant habit: Upright growing stems emerge basally.

Plant spread: Approximately 23 cm.

Height: Approximately 23 cm to top of flowering plane. Approximately 13 cm to top of foliar plane.

Length plant stem: Average range 10 to 13 cm.

Diameter of plant stem: Approximately 0.3 cm.

Quantity stems: Approximately 30.

Stem:

*Color*.—Near RHS Green 139C.

*Texture*.—Smooth.

Internode length: Average 3.2 cm.

Internodes per stem: 3-5.

Stem shape in cross-section: Circular.

Stem hollowness: Absent.

FOLIAGE

Leaf:

*Arrangement*.—Opposite (in pairs).

*Quantity*.—Approximately 6-12 fully expanded per stem. Average range of 4 to 6 immature leaves per stem.

*Average length*.—Approximately 4.5 cm.

*Average width*.—Approximately 0.7 cm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Curvature*.—Moderately recurved.

*Glaucosity*.—Weak.

*Color*.—Young foliage upper side: Near RHS Green 136A. Young foliage under side: Near RHS Green 136A. Mature foliage upper side: Near RHS Green 139A. Mature foliage under side: Near RHS Green 136A.

*Venation*.—Type: Linear with a prominent mid vein. Venation color upper side: Indistinguishable from foliage. Venation color under side: Indistinguishable from foliage.

FLOWER

Natural flowering season: Perpetual flowering.

Inflorescence type and habit: Umbel of 2 flowers, or single occurring flowers.

Flower longevity on plant: 2-3 weeks.

Quantity of flowers: Approximately 40 flowers on a 20 week old plant.

Flowers persistent or self cleaning: Persistent.

Fragrance: Faint to moderate sweet scent.

Inflorescence size:

*Diameter*.—Approximately 5.0 cm.

*Height*.—Approximately 3.5 cm.

Individual flower size:

*Diameter*.—Approximately 3.0 cm.

*Length*.—Approximately 2.5 cm.

Petals, excluding tube:

*Petal arrangement*.—Whorled, multiple whorl.

*Shape*.—Spatulate, with an elongated narrow base and orbicular distal section.

*Base*.—Attenuate.

*Margin*.—Serrated.

*Depth of serrated margin*.—Shallow.

*Number of incisions in margin*.—Moderate.

*Apex*.—Serrated.

*Length*.—2.5 cm.

*Width*.—1.1 cm.

*Petal quantity*.—Average range 15 to 20.

*Texture*.—Smooth all surfaces.

*Aspect*.—Flat to slightly undulating.

Color:

*When opening*.—Upper surface: Near RHS Red-Purple 71B Base near White N155B. Lower surface: Near RHS Purple 75A. Base near White N155B.

*Fully opened*.—Upper surface: Near RHS Red-Purple 71B Base near White N155B. Lower surface: Near RHS Red-Purple N74C Base near White N155B.

*Fading*.—Upper surface: Near RHS Purple 77B. Base near White N155B. Lower surface: Near RHS Purple-Violet N80D. Base near White N155B.

Tube:

*General description*.—Tube consists of the elongated, unfused base of the petals. Tube shape caused by a fused cylindrical calyx.

*Length*.—1.7 cm.

*Width*.—0.7 cm.

*Texture*.—Smooth.

Color:

*Fully opened*.—Inner surface: Near RHS Green 138A. Outer surface: Near RHS Green 137C.

Bud:

*Shape*.—Elongated cylinder.

*Length*.—Average 1.7 cm.

*Diameter*.—Average 0.7 cm.

*Color*.—Near RHS Green 139B.

Sepals:
*Quantity.*—5.
*Arrangement.*—Fused tube.
*Shape.*—Acute.
*Length.*—1.8 cm.
*Width.*—0.4 cm.
*Margin.*—Entire.
*Apex.*—Acute.
*Texture.*—Smooth upper and lower surfaces.
*Color, upper and lower surfaces.*—Near RHS Green 138A.

Bracteoles:
*Shape.*—Deltate.
*Quantity per flower.*—4.
*Length.*—Approximately 0.7 cm.
*Width.*—Approximately 0.5 cm.
*Margin.*—Entire.
*Texture.*—Smooth, upper and lower surfaces.
*Color.*—Near RHS Green 137A, upper and lower surfaces.

Peduncle:
*Length.*—Average 1.8 cm.
*Diameter.*—0.2 cm.
*Color.*—Near RHS Green 138A.
*Orientation.*—Upright.
*Strength.*—Flexible.
*Texture.*—Smooth.

Pedicel:
*Length.*—Average 0.8 cm.
*Diameter.*—0.2 cm.
*Color.*—Near RHS Green 138A.
*Orientation.*—Upright.
*Strength.*—Flexible, elastic.

REPRODUCTIVE ORGANS

Stamens:
*Number.*—Most commonly 4.
*Filament length.*—Approximately 0.4 cm.

Anthers:
*Shape.*—Oblong.
*Length.*—Approximately 0.1 cm.
*Color.*—Near RHS White 155A.
*Pollen.*—Not observed.

Pistil:
*Number.*—3.
*Length.*—Approximately 2.2 cm.
*Style.*—Length: Approximately 1.3 cm. Color: Near RHS White N155B. Bud style extrusion before opening: Approximately 5 mm.

Stigma:
*Shape.*—Linear, arching.
*Color.*—Near RHS White N155B.
*Ovary shape.*—Oblong.
*Ovary diameter.*—0.4 cm.
*Ovary length.*—0.9 cm.
*Ovary color.*—Near RHS Yellow-Green 145B.
*Ovary surface texture.*—Smooth.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: Alternaria dianthicola, Botrytis cinerea, Erwinia chrysanthemi, Pseudomonas caryophylli, Fusarium graminearum, Fusarium avenaceum, Fusarium culmorum and Rhizoctonia solani, Typical pests include; various species of *Thysanopthera*, various *Aphis* species, and various species of *Tetranychus.*

Temperature tolerance: USDA zones 3 through 10 tolerant.

What is claimed is:

1. A new and distinct cultivar of *Dianthus* plant named 'DCACA06-0' as herein illustrated and described.

* * * * *